United States Patent [19]

Wheeler

[11] 4,259,485

[45] Mar. 31, 1981

[54] CRYSTALLIZATION PROCESS

[75] Inventor: William J. Wheeler, Indianapolis, Ind.

[73] Assignee: Eli Lilly and Company, Indianapolis, Ind.

[21] Appl. No.: 32,840

[22] Filed: Apr. 24, 1979

[51] Int. Cl.³ .......................................... C07D 413/02
[52] U.S. Cl. ................................. 544/90; 424/248.52
[58] Field of Search .......................................... 544/90

[56] References Cited

U.S. PATENT DOCUMENTS 4,138,486  2/1979  Narisada et al. ................... 544/90 X
4,201,782  5/1980  Narisada et al. ................... 544/90 X

OTHER PUBLICATIONS

Hawley, The Condensed Chemical Dictionary, Ninth Edition, p. 770, Van Nostrand Reinhold Co., NY, copyright ed. 1977.

Grant, Hackh's Chemical Dictionary, 4th Ed., p. 606, McGraw-Hill Book Co., NY, copyrighted 1969.

*Primary Examiner*—John D. Randolph
*Attorney, Agent, or Firm*—William B. Scanlon; Arthur R. Whale

[57] ABSTRACT

The crystalline D-sesquisodium salt of the diacid of the formula

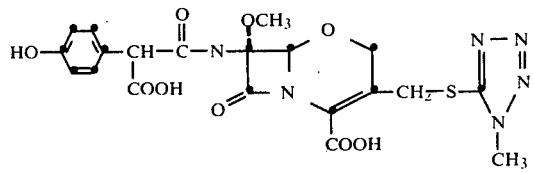

and process for its preparation via acetone dilution of an aqueous solution of non-crystalline D,L-diacid and D,L-disodium salt.

4 Claims, No Drawings

CRYSTALLIZATION PROCESS

BACKGROUND OF THE INVENTION

This invention relates to the crystalline, substantially pure, D isomer of the sesquisodium salt of the oxa-β-lactam antibiotic diacid represented by the following structural formula I,

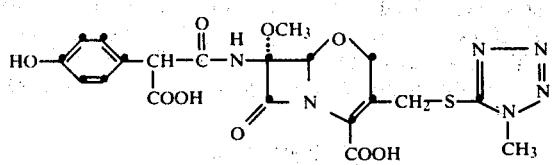

and to a process for the preparation thereof.

The antibiotic has been previously described, U.S. Pat. No. 4,138,486 issued Feb. 6, 1979, and is highly effective in the treatment of infectious diseases caused by both gram-positive and gram-negative bacteria. The antibiotic is one member of a class of antibiotics which have structural features in common with the cephalosporin class of antibiotics, however, they differ from the cephalosporins chemically and biologically. Structurally they differ primarily by having an oxygen atom in place of the sulfur atom of the cephalosporins. Further, the oxa-β-lactams are prepared by methods differing from those by which the semi-synthetic cephalosporin antibiotics are prepared. Biologically they differ primarily from the cephalosporins by exhibiting generally high potency against pseudomonas and other gram-negative bacteria.

The compound of the formula I as the disodium salt having the D,L configuration about the chiral center in the α-carboxy-(4-hydroxyphenylacetyl side chain has been prepared previously. However, the D-epimer and a method for its preparation have thus far not been described. Further, the known preparations of the disodium salt have been non-crystalline amorphous solids with stability characteristics which render it unsuitable for pharmaceutical formulations.

The disodium salt of the D,L diacid of the formula I is formally named 7β-[DL-[carboxy(4-hydroxyphenyl)acetyl]amino]-7α-methoxy-3[[(1-methyl-1H-tetrazol-5-yl)thio]methyl]-8-oxo-5-oxa-1-azabicyclo[4.1.0]oct-2-ene-2-carboxylic acid disodium salt. For convenience herein the disodium salt is referred to as the oxa-β-lactam disodium salt and the free diacid as the oxa-β-lactam diacid.

The D-epimer of the sesquisodium salt demonstrates higher antibiotic activity than the D,L-disodium salt against some organisms (e.g. E. coli).

DETAILED DESCRIPTION

The D-sesquisodium salt of the diacid of formula I is obtained as crystalline needles melting at about 175° C. to about 180° C. with decomposition. Its ultraviolet absorption spectrum run in methyl alcohol shows absorption maxima at 228 nm ($\epsilon$, 17,300) and 270 nm ($\epsilon$, 11,800).

The ratio of D-epimer to L-epimer in the sesquisodium salt obtained in the process is determined by high performance liquid chromatography (HPLC) and varies from about 93% to about 98% D epimer.

The characterization of the salt form obtained in the process as the sesquisodium salt is based on the product's atomic absorption, elemental analysis and titration. The percent sodium content of the sesquisodium salt by calculation is 5.56. The percent sodium observed by atomic absorption and correcting for water content (Karl Fischer water determination) and the presence of any acetone in the product was within experimental error, although variable from crystallization to crystallization.

The D-sequisodium salt in water gave an initial pH of 3.8 and on titration in water three pKa values were observed as follows: $pKa_1$ 2.5, $pKa_2$ 3.7, and $pKa_3$ 10.2.

The D-1-oxa-β-lactam sesquisodium salt of this invention provides a pharmaceutically useful crystalline form which can be used in the preparation of formulations for parenteral administration.

The D-epimer of the oxa-β-lactam sesquisodium salt is prepared by the process of this invention with the amorphous D,L-disodium salt and the D,L-oxa-β-lactam diacid. According to the process of this invention, a mixture of the D,L-diacid of the formula I and the D,L-disodium salt is dissolved in water at a temperature between about 15° C. and about 35° C. and the solution is diluted with acetone until the solution reaches the cloud point. The solution is then cooled to the crystallization temperature of between about −35° C. and about −10° C. until crystallization of the D-epimer sesquisodium salt occurs. The crystalline sesquisodium salt is separated from the cold solution and is washed with a suitable solvent such as acetone or diethyl ether and dried.

The crystallization of the D-epimer sesquisodium salt is enhanced by seeding the cold aqueous solution at the cloud point with sesquisodium salt D-epimer.

The filtrate remaining after the D-sesquisodium salt is separated can be reused in the process to obtain additional D-epimer. The filtrate is diluted with acetone again to the cloud point and chilled to the crystallization temperature to obtain additional D-sesquisodium salt.

The D,L-oxa-β-lactam diacid and the D,L-disodium salt thereof can be mixed together in various proportions in the solid state prior to dissolution in water, or they can be dissolved separately in water and the solutions mixed. Alternatively the solution of the diacid and disodium salt for use in the process can be prepared by adding from about 1 equivalent to about 1.5 equivalents of sodium hydroxide to a suspension of the amorphous D,L-diacid in water. The D,L-diacid is partially soluble in water. The resulting solution is then diluted with acetone and cooled to the crystallization temperature according to the process of this invention.

Although the concentration of the aqueous solution of the D,L-diacid and D,L-disodium salt does not appear to be critical, higher yields of the D-sesquisodium salt are obtained when the concentration of the solution is from about 0.1 g to about 1 g of combined weight of the D,L-diacid and D,L-disodium salt per milliliter of water.

As was mentioned above, the D,L diacid and the D,L-disodium salt can be present in solution in varying proportions relative to each other. In the process the mole ratio of D,L-disodium salt to the D,L-diacid in solution can be from about 1:1 to about 6:1. At higher ratios of the disalt to diacid the D,L-disodium salt may co-precipitate with the desired D-sesquisodium salt. The preferred ratio is from about 1 to about 2 moles of the D,L-disodium salt to 1 mole of the D,L-diacid.

On dilution of the aqueous solution of the D,L-disodium salt and the D,L-diacid with acetone the cloud point is reached when the diluted solution contains about 80% to about 90% acetone by volume.

The crystals of the D-sesquisodium salt obtained in the process are solvated with acetone. The acetone is present in the solvate at approximately a 1:1 ratio to the sesquisodium salt. The acetone is loosely bound to the crystals of the sesqui salt and most can be removed by evaporation under vacuum.

The acetone used in the process serves as an antisolvent and also in the formation of the crystalline solvate and thus aids in the formation of the crystalline sesquisodium salt.

The purity of the D-sesquisodium salt can be enhanced by recrystallization under the process conditions of this invention. For example, the D-sesquisodium salt is dissolved in water and the solution diluted with acetone to the cloud point. On standing at the crystallization temperature, D-sesquisodium salt reprecipitates as crystalline needles solvated with acetone.

The process of this invention provides the crystalline D-sesquisodium salt substantially free of the L-epimer. The term "substantially free of L-epimer" when used herein refers to crystalline sesquisodium salt containing 90% or greater of the D-epimeric form.

As noted previously herein, the ratio of the D-epimer to the L-epimer in the crystalline sesquisodium salt was determined by High Performance Liquid Chromatography (HPLC). The HPLC system used was as follows:

Column: Water's Associates Bonapak C-18
Flow rate: 3 ml/min
Solvent: 0.1 N ammonium acetate, 100 parts methyl alcohol, 6 parts
Sample solvent: phosphate buffer, pH 7.4
Sample concentration: 1 mg/ml
Sample volume: 15 microliters The following examples further describe the process and composition of the invention.

EXAMPLE 1

A mixture of 0.5 g of the oxa-β-lactam diacid and 0.5 g of the amorphous disodium salt was dissolved in 1.5 ml of water and acetone was added portionwise to the solution at room temperature until a slight cloudiness persisted. The solution was chilled, seeded with crystals of the D sodium salt and stored at a temperature of about −20° C. for several hours. The crystalline D-sesquisodium salt which precipitated from the cold solution were collected by filtration, were washed with acetone and dried in vacuo. The dried crystalline needles weighed 0.257 g. The crystals melted with decomposition at about 175° C. to about 180° C.

Analysis by high pressure liquid chromatography showed the crystalline material was 93% D-epimer and 7% L-epimer.

EXAMPLE 2

A solution of 2.5 g of the D,L-oxa-β-lactam disodium salt and 2.5 g of the D,L-oxa-β-lactam diacid in 5 ml of water was diluted at room temperature with acetone until the cloud point was reached. The slightly turbid solution was cooled to −20° C. for crystallization. The crystalline D-oxa-β-lactam sesquisodium salt was collected by filtration, washed with diethyl ether and dried. The dried crystals weighed 2.77 g.

The filtrate was diluted with acetone to the cloud point and stored at −20° C. The second crop of D-sesquisodium salt obtained weighed 0.249 g. The crystalline product contained 7.7% water (Karl Fischer) and was 96.7% D (HPLC).

EXAMPLE 3

A solution of 0.6 g of the D,L-oxa-β-lactam disodium salt and 0.3 g of the D,L-diacid (ratio 2:1) in 0.9 ml of water was diluted with acetone to the cloud point and then allowed to stand for crystallization at about −20° C. The crystals of D-sesquisodium salt were filtered, washed and dried. The crystalline product weighed 0.55 g.

EXAMPLE 4

Recrystallization of D-oxa-β-lactam sesquisodium salt

A solution of 2.068 g. of the D-sesquisodium salt in 2 ml of water was diluted with acetone to the cloud point and then allowed to stand at about −20° C. after seeding. The first crop of D-sesquisodium salt was collected by filtration, washed and dried. The colorless crystalline product weighed 960 mg.

The following analytical data were obtained with the recrystallized D-sesquisodium salt.

Microanalysis for $C_{20}H_{19}N_6O_9SNa_{1.5}\cdot1H_2O$: Calculated: C, 41.99; H, 3.67; N, 14.69. Found: C, 42.00; H, 3.19; N, 14.52.

Sodium by atomic absorption: Calculated: Na, 5.56 (corrected for 7.4% water and 5% acetone). Found: Na, 5.49

D/L ratio (HPLC): D, 95.7%; L, 4.3%.

Titration ($H_2O$): Initial pH 3.8; $pKa_1$, 2.5; $pKa_2$, 3.7; $pKa_3$, 10.2.

On titration, the sample of the sesquisodium salt required 0.5 equivalents of sodium hydroxide to complete the titration from pH 3.7 to pH 5.7.

Apparent Molecular Weight (titration): 563.
Residual solvents (NMR): acetone, 5.15%.
Water content (Karl Fischer): 7.36%.
Specific rotation:
$[\alpha]_D^{25} = -18.05$ (pH 7.0 buffer).
$[\alpha]_{365}^{25} = -111.53$ (pH 7.0 buffer).

EXAMPLE 5

To a solution of one gram (1.92 mmole) of amorphous D,L-diacid in 0.48 ml of water were added 2.28 ml of 1 N sodium hydroxide (2.28 mmole). After the base was added the solution was diluted with acetone to the cloud point and chilled at a temperature of about −20° C. The cold solution was seeded with crystals of the D-sesquisodium salt and allowed to stand in the cold. The D-sesquisodium salt crystallized and was filtered and dried. The crystals weighed 0.441 g.

I claim:

1. The D-sesquisodium salt of the oxa-β-lactam diacid of the formula

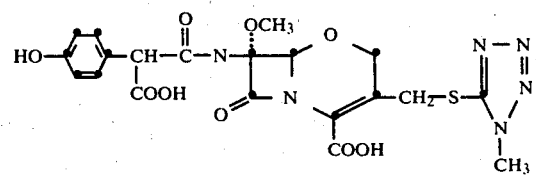

substantially free of the L form.

2. The acetone solvate of the salt of claim 1.

3. The process for preparing the D-sesquisodium salt of claim 1 which comprises (1) adding acetone to a water solution containing the D,L-disodium salt of the formula

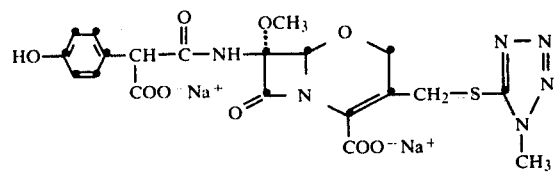

and the D,L-diacid of the formula

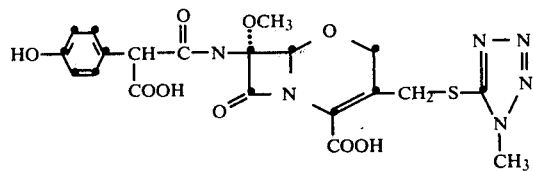

in a molar ratio of the disalt to the diacid of between about 1 to 1 to about 6 to 1, and (2) cooling the solution to a temperature between about −35° C. and about −10° C.

4. The process of claim 3 wherein the molar ratio of D,L-disodium salt to the D,L-diacid is 1:1 or 2:1.

* * * * *

UNITED STATES PATENT AND TRADEMARK OFFICE
CERTIFICATE OF CORRECTION

PATENT NO. : 4,259,485

DATED : March 31, 1981

INVENTOR(S) : William J. Wheeler

It is certified that error appears in the above—identified patent and that said Letters Patent is hereby corrected as shown below:

Column 4, line 57, "The D-sesquisodium" should read -- The crystalline D-sesquisodium --; line 62, that part of the structural formula reading " 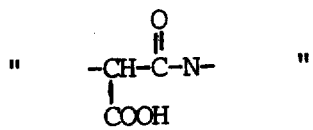 "

should read

-- 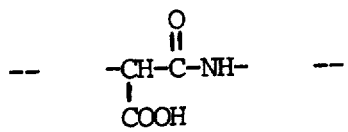 --

Column 5, line 12, that part of the structural formula reading

" 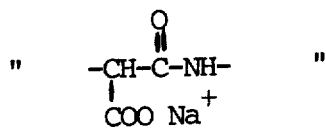 "

should read

UNITED STATES PATENT AND TRADEMARK OFFICE
CERTIFICATE OF CORRECTION

PATENT NO. : 4,259,485

DATED : March 31, 1981

INVENTOR(S) : William J. Wheeler

It is certified that error appears in the above—identified patent and that said Letters Patent is hereby corrected as shown below:

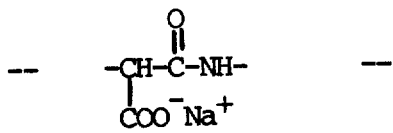

Column 6, line 3, that part of the structural formula reading

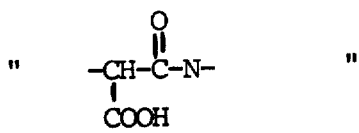

should read

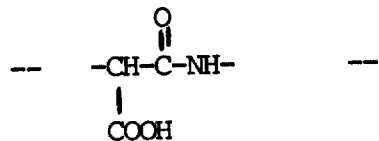

[SEAL]

Attest:

Attesting Officer

Signed and Sealed this

Eighteenth Day of January 1983

GERALD J. MOSSINGHOFF

Commissioner of Patents and Trademarks